United States Patent
Eizenhöfer

(10) Patent No.: US 6,926,680 B2
(45) Date of Patent: Aug. 9, 2005

(54) COUPLING BELLOWS FOR SHOCKWAVE THERAPY

(75) Inventor: Harald Eizenhöfer, Seefeld (DE)

(73) Assignee: Dornier MedTech Systems GmbH, Wessling (DE)

( * ) Notice: Subject to any disclaimer, the term of this patent is extended or adjusted under 35 U.S.C. 154(b) by 0 days.

(21) Appl. No.: 10/461,928

(22) Filed: Jun. 13, 2003

(65) Prior Publication Data

US 2004/0068210 A1 Apr. 8, 2004

Related U.S. Application Data

(63) Continuation of application No. PCT/DE01/04710, filed on Dec. 12, 2001.

(30) Foreign Application Priority Data

Dec. 15, 2000 (DE) .......................... 100 62 749

(51) Int. Cl.⁷ .............................................. A61B 17/22
(52) U.S. Cl. ............................................... 601/4; 601/2
(58) Field of Search .............................. 601/2, 3, 4, 46, 601/148; 600/439; 367/140, 152, 175; 381/71.1, 71.7, 71.8

(56) References Cited

U.S. PATENT DOCUMENTS

| | | | |
|---|---|---|---|
| 4,798,196 A | | 1/1989 | Nowacki et al. |
| 4,962,752 A | * | 10/1990 | Reichenberger et al. ........ 601/4 |
| 5,046,483 A | * | 9/1991 | Ogura ............................ 601/4 |
| 5,070,861 A | * | 12/1991 | Einars et al. ................... 601/4 |
| 5,072,723 A | * | 12/1991 | Viebach .......................... 601/4 |
| 5,394,786 A | * | 3/1995 | Gettle et al. .................... 86/50 |
| 5,450,848 A | * | 9/1995 | Okazaki et al. ............. 600/439 |
| 5,810,748 A | * | 9/1998 | Ueberle .......................... 601/4 |

FOREIGN PATENT DOCUMENTS

| | | | |
|---|---|---|---|
| DE | 139823 A1 * | 5/1985 | .......... F16L/55/02 |
| DE | 9102394 | 6/1991 | |
| DE | 19509004 | 10/1996 | |
| DE | 29712035 | 10/1997 | |
| DE | 19625164 | 1/1998 | |
| EP | 0445322 | 9/1991 | |

* cited by examiner

*Primary Examiner*—Danton D. DeMille
*Assistant Examiner*—Quang D. Thanh
(74) *Attorney, Agent, or Firm*—King & Spalding LLP

(57) ABSTRACT

An apparatus for coupling a shockwave source to the body of a patient is provided. The apparatus may include a coupling bellows that is configured to rotate about an axis of rotation. The coupling bellows may include a coupling portion that is configured to provide a coupling surface relative to the body of a patient and is transmissive to shockwaves. The coupling bellows may also include an outer portion that is sound-insulating.

10 Claims, 1 Drawing Sheet

US 6,926,680 B2

COUPLING BELLOWS FOR SHOCKWAVE THERAPY

CROSS-REFERENCE TO RELATED APPLICATION

This application is a continuation, under 35 U.S.C. § 365(c), of the co-pending PCT patent application entitled "Coupling Bellows for Shockwave Therapy," having International Application No. PCT/DE01/04710, International Filing Date 12 Dec. 2001 (Dec. 12, 2001), and Priority Date 15 Dec. 2000 (Dec. 15, 2000), which claims priority to German Patent Application No. 100 62 749.8, filed on Dec. 15, 2000, and which is entirely incorporated herein by reference. Therefore, this application claims the benefit of the Dec. 15, 2000 filing date of German Patent Application No. 100 62 749.8, based on the foregoing chain of co-pendency.

FIELD OF THE INVENTION

The present invention generally relates to the application of shockwave therapy to a patient, and more particularly, to an apparatus used for coupling a shockwave source to the body of a patient.

BACKGROUND OF THE INVENTION

In shockwave therapy, an objectionable airborne sound, which is subjectively noticed as a loud "shot," can be created with each shockwave. This source of noise can be considered by a patient, and also by the treating personnel, as a burden.

Typically, the foregoing objectionable airborne sound is mainly emitted from the area of the coupling bellows (of a shockwave therapy device) that is not covered by a patient's body. Existing approaches have provided additional noise-insulating material on the outer lateral surface of the coupling bellows, such as towels, small sand bags, or specifically designed sound-insulating sleeves.

However, existing approaches, such as the foregoing, have shortcomings. For example, such existing approaches are typically difficult to handle and/or are heavy. As another example, such existing approaches typically present an obstacle in the locating of a concrement in a patient by extending into the optical path of the X-ray device or the ultrasonic device associated with the shockwave therapy treatment.

In light of the foregoing, there is a need in the art for an apparatus for coupling a shockwave source to the body of a patient, that emits less of an objectionable airborne sound without restricting the locating of a concrement in a patient and without being heavy or otherwise difficult to handle.

SUMMARY OF THE INVENTION

The present invention is generally directed to an apparatus for coupling a shockwave source to the body of a patient. In one aspect, the invention provides a coupling bellows that has substantial rotational symmetry with an axis of rotation. The coupling bellows may include a coupling portion that provides a coupling surface relative to the body of a patient and is transmissive to shockwaves. The coupling bellows may also include an outer portion that comprises a sound-insulating filler.

These and other aspects of the invention will be described further in the detailed description below in connection with the drawings and the claims.

BRIEF DESCRIPTION OF THE DRAWINGS

The accompanying drawings are incorporated into and form a part of the specification for the purpose of explaining the principles of the invention. The drawings are not to be construed as limiting the invention to only the illustrated and described examples of how the invention can be made and used. Further features and advantages will become apparent from the following, and more particular description of the invention as illustrated in the accompanying drawings, wherein.

DETAILED DESCRIPTION OF THE INVENTION

Figure 1:
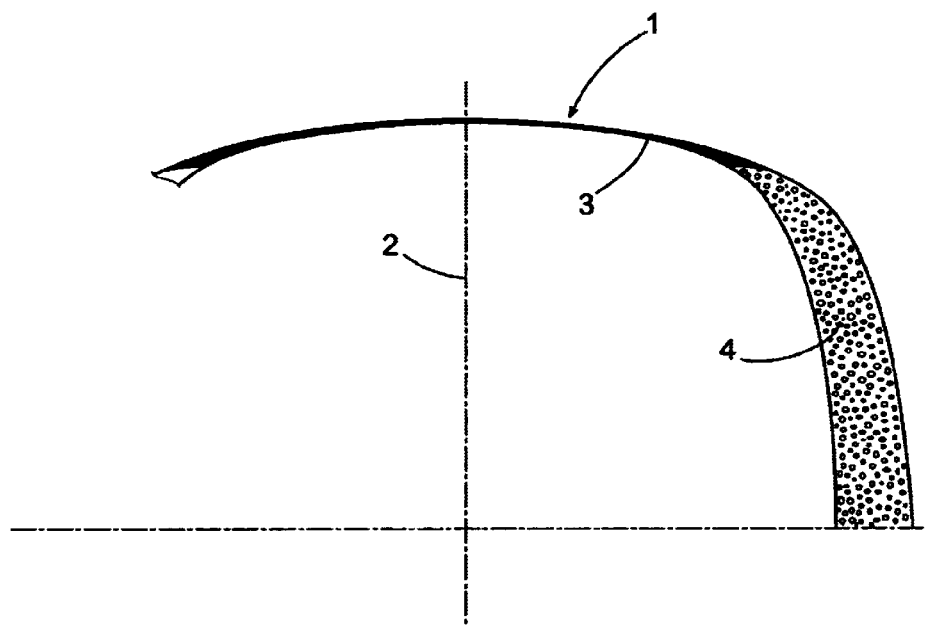
FIG. 1 is a diagram illustrating an exemplary embodiment of the coupling bellows of the present invention.

The illustrative embodiments of the present invention will be described with reference to the drawings, wherein like elements and structures are indicated by like reference numbers. In this regard, reference is made to FIG. 1, which illustrates an exemplary embodiment of the coupling bellows 1 in a sectional view. The construction of the coupling bellows 1 is substantially in rotational symmetry with the axis 2. The coupling portion 3 that comes into contact with a patient (not depicted) is thin-walled and is without inclusions. The shockwaves produced a by a shockwave source are, thus, only absorbed to a minimum degree. By contrast, the lateral outer portion 4 is designed for maximum sound absorption by way of air pores or other fillers.

The use of air pores in the lateral outer portion 4 provides the additional advantage of making the coupling bellows 1 more elastic and able to adapt to different penetration depths (e.g., along axis 2). Therefore, the coupling bellows 1 are elastic and can adapt to penetration depths along axis 2, which each require a different extension of the coupling bellows, in a better way than a homogenous material without pores.

Preferably, although not exclusively, the coupling bellows 1 are produced using a so-called "compression molding" method. In such method, one or more partly vulcanized mats that have been cut to size are inserted into a tool as "blanks." Under the action of pressure and temperature in the tool, the blanks become paste-like to liquid in composition, thereby connecting to each other and then curing completely.

According to an exemplary embodiment of the present invention, a material which develops pores during vulcanization or polymerization (e.g., sponge rubber) is chosen to produce the lateral outer portion 4, whereby the insertion part for the coupling portion 3 exhibits optimum shockwave and ultrasound transmission. Most elastomers, such as the large class of rubber materials, are suited as such a material. Additionally, silicones and polyurethanes may also be used.

While the invention has been described with respect to the foregoing exemplary embodiments, it will be apparent to those skilled in the art that various modifications, variations and improvements of the invention may be made in light of the above teachings and within the purview of the appended claims without departing from the spirit and intended scope of the invention. In regard to the foregoing description of the exemplary embodiments of the invention, areas which are known to those of ordinary skill in the art have not been described in detail in order to facilitate a clear and concise description of the invention. Accordingly, it should be understood that the invention is not to be limited by the specific exemplary embodiments, but only by the scope of the appended claims.

What is claimed is:

1. An apparatus for coupling a shockwave source to the body of a patient, comprising:
   a coupling bellows having substantial rotational symmetry with an axis of rotation, said coupling bellows comprising:

a coupling portion disposed substantially perpendicular to the axis of rotation and which provides a coupling surface relative to the body of a patient, said coupling portion being transmissive to shockwaves; and an outer portion disposed adjacent to said coupling portion and having a substantially cylindrical shape relative to the axis of rotation, wherein said outer portion comprises a sound-insulating filler.

2. The apparatus of claim 1, wherein said coupling portion and said outer portion comprise different materials and are coupled together in a liquid-tight manner.

3. The apparatus of claim 2, wherein said outer portion comprises at least one material that becomes porous during one of vulcanization, compression molding, and polymerization.

4. The apparatus of claim 1, wherein said coupling portion and said outer portion comprise vulcanized material.

5. The apparatus of claim 4, wherein said outer portion comprises at least one material that becomes porous during one of vulcanization, compression molding, and polymerization.

6. The apparatus of claim 1, wherein said sound-insulating filler comprises air pores.

7. The apparatus of claim 6, wherein said coupling portion and said outer portion comprise different materials and are coupled together in a liquid-tight manner.

8. The apparatus of claim 7, wherein said outer portion comprises at least one material that becomes porous during one of vulcanization, compression molding, and polymerization.

9. The apparatus of claim 6, wherein said coupling portion and said outer portion comprise vulcanized material.

10. The apparatus of claim 9, wherein said outer portion comprises at least one material that becomes porous during one of vulcanization, compression molding, and polymerization.

* * * * *